US012622822B2

(12) United States Patent
Lambertz et al.

(10) Patent No.: US 12,622,822 B2
(45) Date of Patent: May 12, 2026

(54) ABSORBENT ARTICLE FOR LIQUID STOOL MANAGEMENT

(71) Applicants: ONTEX BV, Buggenhout (BE); ONTEX GROUP NV, Erembodegem (BE)

(72) Inventors: Christina Lambertz, Neuwied (DE); Katharina Sprotte, Koblenz (DE); Agnes Dominika Reuter, Cologne (DE)

(73) Assignees: Ontex BV, Buggenhout (BE); Ontex Group NV, Erembodegem (BE)

( * ) Notice: Subject to any disclaimer, the term of this patent is extended or adjusted under 35 U.S.C. 154(b) by 349 days.

(21) Appl. No.: 18/574,557

(22) PCT Filed: Jun. 24, 2022

(86) PCT No.: PCT/EP2022/067427
§ 371 (c)(1),
(2) Date: Dec. 27, 2023

(87) PCT Pub. No.: WO2023/274892
PCT Pub. Date: Jan. 5, 2023

(65) Prior Publication Data
US 2024/0293269 A1      Sep. 5, 2024

(30) Foreign Application Priority Data
Jun. 28, 2021    (EP) ..................................... 21182187

(51) Int. Cl.
*A61F 13/533* (2006.01)
*A61F 13/49* (2006.01)
(Continued)

(52) U.S. Cl.
CPC ...... *A61F 13/53708* (2013.01); *A61F 13/533* (2013.01); *A61F 13/53747* (2013.01);
(Continued)

(58) Field of Classification Search
CPC .............. A61F 13/53708; A61F 13/533; A61F 13/53747; A61F 2013/4958; A61F 2013/5315
See application file for complete search history.

(56) References Cited

U.S. PATENT DOCUMENTS 5,554,243 A * 9/1996 Igaue .................... A61F 13/531
                                                    156/324
5,665,083 A * 9/1997 Igaue .................... A61F 13/531
                                                    428/137
(Continued)

FOREIGN PATENT DOCUMENTS

EP        3711730 A1    9/2020
EP        3861970 A1    8/2021
(Continued)

OTHER PUBLICATIONS

International Search Report and Written Opinion for PCT/EP2022/067427, mailed Sep. 26, 2022.

*Primary Examiner* — Guy K Townsend
(74) *Attorney, Agent, or Firm* — VIVICAR Law, PLLC

(57) ABSTRACT

The current invention concerns an absorbent article (10) comprising an absorbent core (12) sandwiched between a liquid permeable topsheet (14) and a liquid impermeable backsheet (16), and an acquisition distribution layer (18) arranged between said topsheet (14) and said absorbent core (12), wherein the absorbent core (12) comprises at least an absorbent material layer. According to the invention the topsheet (14) consists essentially of an air-through bonded nonwoven layer and is free of spunbond nonwoven layers, the acquisition distribution layer (18) comprises a spunbonded and/or thermocarded nonwoven layer, and the absorbent core (12) comprises at least one channel (26) free of (Continued)

absorbent material. The invention also relates to the use of such an absorbent article (10), for managing liquid stool.

12 Claims, 1 Drawing Sheet

(51) Int. Cl.
    *A61F 13/53*     (2006.01)
    *A61F 13/537*    (2006.01)
    *A61F 13/495*    (2006.01)
    *A61F 13/531*    (2006.01)

(52) U.S. Cl.
    CPC ................. *A61F 2013/4958* (2013.01); *A61F 2013/5315* (2013.01)

(56)                    References Cited

U.S. PATENT DOCUMENTS

| | | | | | |
|---|---|---|---|---|---|
| 6,245,051 | B1 * | 6/2001 | Zenker | ................ | A61F 13/5376 604/385.23 |
| 6,395,955 | B1 | 5/2002 | Roe et al. | | |
| 6,437,214 | B1 * | 8/2002 | Everett | .............. | A61F 13/5376 604/378 |
| 6,673,982 | B1 * | 1/2004 | Chen | ................ | A61F 13/53743 604/385.101 |
| 7,745,687 | B2 * | 6/2010 | Heyn | ................ | A61F 13/15626 604/378 |
| 8,206,533 | B2 * | 6/2012 | Hundorf | ................... | B32B 5/30 156/305 |
| 8,216,666 | B2 * | 7/2012 | Warner | ............ | A61F 13/51496 428/323 |
| 8,658,852 | B2 * | 2/2014 | Paldey | ................. | A61F 13/539 604/379 |
| 8,748,693 | B2 * | 6/2014 | Westwood | ............. | B32B 5/028 604/383 |
| 11,273,083 | B2 * | 3/2022 | Bewick-Sonntag | ........................ | A61F 13/15699 |
| 11,285,056 | B2 * | 3/2022 | Erdem | ..................... | B32B 7/09 |
| 12,357,515 | B2 * | 7/2025 | Van Malderen | .... | A61F 13/5323 |
| 12,404,434 | B2 * | 9/2025 | Turner | .................... | C08L 23/26 |
| 2007/0043330 | A1 * | 2/2007 | Lankhof | .......... | A61F 13/51394 604/378 |

| | | | | | |
|---|---|---|---|---|---|
| 2009/0137975 | A1 * | 5/2009 | Kohira | ..................... | D04H 3/11 604/385.01 |
| 2012/0238984 | A1 * | 9/2012 | Paldey | .................. | A61F 13/539 604/378 |
| 2013/0046263 | A1 * | 2/2013 | Fukudome | ............. | B32B 5/022 604/375 |
| 2014/0005622 | A1 * | 1/2014 | Wirtz | .................... | A61F 13/539 604/366 |
| 2014/0005623 | A1 * | 1/2014 | Wirtz | ............... | A61F 13/53418 604/366 |
| 2014/0163500 | A1 * | 6/2014 | Roe | ................... | A61F 13/49001 604/374 |
| 2014/0163501 | A1 * | 6/2014 | Ehmsperger | ........... | A61F 13/49 604/374 |
| 2014/0163506 | A1 * | 6/2014 | Roe | ........................ | A61F 13/535 604/378 |
| 2014/0163511 | A1 * | 6/2014 | Roe | ........................ | A61F 13/532 604/385.101 |
| 2014/0303582 | A1 * | 10/2014 | Wright | .............. | A61F 13/15658 156/60 |
| 2015/0005727 | A1 * | 1/2015 | Matsushita | ............. | A61L 15/26 442/382 |
| 2015/0065976 | A1 * | 3/2015 | Roe | ........................ | A61F 13/42 604/374 |
| 2015/0080821 | A1 * | 3/2015 | Peri | ......................... | C08J 3/245 604/385.01 |
| 2016/0136014 | A1 * | 5/2016 | Arora | ...................... | B32B 5/022 |
| 2016/0354260 | A1 * | 12/2016 | Roe | ...................... | A61F 13/532 |
| 2017/0156947 | A1 * | 6/2017 | Esquerra | .............. | A61F 13/496 |
| 2017/0281425 | A1 * | 10/2017 | Herfert | ................ | A61F 13/535 |
| 2017/0312149 | A1 * | 11/2017 | Bianchi | ................ | A61F 13/537 |
| 2019/0192354 | A1 * | 6/2019 | Bewick-Sonntag | .... | A61F 13/47 |
| 2019/0240084 | A1 * | 8/2019 | Rosati | ................... | A61F 13/513 |
| 2020/0078230 | A1 | 3/2020 | Mccormick et al. | | |
| 2020/0108168 | A1 * | 4/2020 | Turner | ................ | D04H 1/5405 |
| 2020/0299880 | A1 | 9/2020 | Ashraf | | |
| 2020/0330291 | A1 * | 10/2020 | Lindner | ............... | A61F 13/532 |
| 2021/0251823 | A1 * | 8/2021 | Yuan | ................ | A61F 13/15203 |
| 2024/0189163 | A1 * | 6/2024 | Wang | ................. | A61F 13/5605 |

FOREIGN PATENT DOCUMENTS

| | | |
|---|---|---|
| JP | 2019080907 A | 5/2019 |
| WO | 2017053036 A1 | 3/2017 |

* cited by examiner

ABSORBENT ARTICLE FOR LIQUID STOOL MANAGEMENT

TECHNICAL FIELD

The disclosure pertains to the technical field of absorbent articles for hygiene products. In particular, the present disclosure relates to the structure or construction of an absorbent article that can be used for absorbing body fluids and exudates, such as urine and fecal material, or blood, menses, and vaginal fluids. More particularly, the present disclosure relates to absorbent garments, such as disposable diapers or diaper pants, disposable incontinence diapers or pants, and which are configured to collect and contain fecal material and avoid leakage, or sanitary napkins or panty liners, which are configured to collect and contain blood, menses, urine, vaginal fluids and avoid leakage. More particularly, the present disclosure pertains to an improved absorbent article for liquid stool management and the use of said absorbent article for managing liquid stool.

BACKGROUND

Disposable diapers conventionally include a chassis having a liquid permeable topsheet, a liquid impermeable backsheet and an absorbent structure sandwiched between the topsheet and backsheet. The chassis has a front body panel which, in use, extends over the stomach and front hip area of the user, and a rear body panel which, in use, extends over the back and the rear hip area of the user. Each of the body panels has a waist portion such that, when the diaper is fastened around the waist of the user, the waist portions provide a continuous encirclement of the user. In order to fasten the diaper around the waist of a user, a fastening system comprising fastening tabs is commonly employed. Fastening tabs may be provided on side panels which extend from lateral side edges of the diaper chassis. Disposable pants have a similar construction but typically comprise front and back elasticized belts at either end of the absorbent structure and are sealed together at lateral side seams to form an underwear-resembling product that can be worn by a subject by pulling it up over the legs and may be removed either by pulling it down in the opposite direction or by tearing the side seams.

The poo of babies is influenced by their diet whether they are fed formula or breastfed and if they started having solid foods introduced in their diet. As they digest breast milk or formula, the poo is looser and lighter and tends to be liquid stool having a high amount of liquid components with some solid elements. This results in fluid stool which can move unhindered on the surface of the diaper thereby leading to leakage.

Solutions in the past such as in WO2017/53036 A1 have focused on improving the absorbent core by introducing channels free of absorbent material to improve the acquisition distribution of fluids. This solution helps to distribute the bodily fluid throughout the absorbent core but is not adapted to manage liquid stool in particular and cannot prevent leakage incident.

Another strategy such as in U.S. Pat. No. 6,395,955 A1 focused on adding feces modifying agents to increase the viscosity of the liquid stool to dewater and immobilize the feces within the absorbent article thereby limiting leakage incident. Although more efficient to limit leakage incident, this solution implies adding chemical additives in a diaper which can be harmful to wearer as well as detrimental to the environment, these absorbent articles being disposable.

There remains a need for a fast and effective solution for dewatering and immobilizing liquid stool, in order to lock it in the diaper and avoid leakage incident, that is also more environmental friendly.

The invention thereto aims to provide an improved absorbent article and the use of such absorbent article to manage liquid stool efficiently.

SUMMARY OF THE INVENTION

The present invention relates to an absorbent article comprising an absorbent core arranged between a liquid permeable topsheet and a liquid impermeable backsheet, and an acquisition distribution layer arranged between said topsheet and said absorbent core, wherein the absorbent core comprises at least an absorbent material layer. According to the invention, the topsheet consists essentially of an air-through bonded nonwoven layer and is free of spunbond nonwoven layers, the acquisition distribution layer comprises a spunbonded and/or thermocarded nonwoven layer and the absorbent core comprises at least one channel free of absorbent material.

The synergistic combination of these three layers that consists essentially of or comprise: an air-through bonded nonwoven layer, a spunbonded and/or thermocarded nonwoven layer and an absorbent material layer comprising at least one channel free of absorbent material, enables an improved capillary effect or wicking effect. Indeed, the air-through bonded nonwoven fabric is more air permeable, or more porous, than a spunbonded and/or thermocarded nonwoven fabric which is more air permeable, or more porous, than the absorbent material. The liquid stool is thereby naturally drawn towards the absorbent core by capillary effect. The presence of channels in the absorbent core helps to distribute and manage the sudden surge of liquid stool throughout the absorbent core. The absorbent material can be selected from a group consisting of cellulose fibers, superabsorbent polymers and combinations thereof.

According to an embodiment, the at least one channel is an interconnected channel According to an embodiment, the air permeability of the topsheet is greater than air permeability of the acquisition distribution layer and the air permeability of the acquisition distribution layer is greater than the air permeability of the absorbent core.

According to an embodiment, the density of the topsheet is lesser than the density of the acquisition distribution layer and the density of the acquisition distribution layer is lesser than the density of the absorbent core.

According to an embodiment, the mean flow pore size of the topsheet is greater than the mean flow pore size of the acquisition distribution layer and the mean flow pore size of the acquisition distribution layer is greater than the mean flow pore size of the absorbent core.

The invention also pertains to the use of an absorbent article as described herein for managing liquid stool.

By "managing liquid stool" it is implied that the invention pertains to the use of an absorbent article as described herein to reduce run-off or avoid leakage incident. In other terms, "Managing liquid stool" means a dewatering solution to immobilize the liquid stool, provide physical barrier and lock said liquid stool in the absorbent article, i.e. in the absorbent core of the absorbent article such as a diaper.

All of these embodiments mentioned above can be taken individually or in combination.

Further embodiments are described below and in the claims.

DESCRIPTION OF FIGURES

The drawings and figures are illustrative in nature and not intended to limit the subject matter defined by the claims. The following detailed description can be understood when read in conjunction with the following drawings, where like structure is indicated with like reference numerals in which:

DETAILED DESCRIPTION OF THE INVENTION

Figure 1:
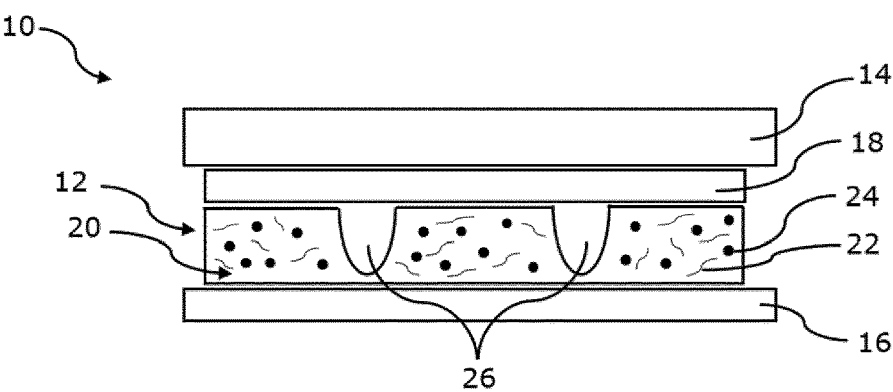
FIG. 1 illustrates a diagrammatic cross section of an absorbent article according to an embodiment.

The current invention concerns an improved absorbent article and the use of such absorbent article to manage liquid stool efficiently.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed disclosure. However, it is to be understood that the value to which the modifier "about" refers is itself also specifically disclosed.

The terms "air permeability" and "relative porosity" are equivalent and refer to the measurement of how easily air can pass through a fabric or material. The measured value may be reported as a speed of air in litre per squared meters per second ($L/m^2/s$).

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" or "% wt" (weight percent), here and throughout the description unless otherwise defined, refers to the relative weight of the respective component based on the overall weight of the formulation, or the relative weight of a material based on the overall weight of the layer.

The recitation of numerical ranges by endpoints includes all numbers and fractions subsumed within that range, as well as the recited endpoints.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious topsheet, a backsheet joined to the topsheet, and an absorbent core positioned and held between the topsheet and the backsheet. The topsheet is operatively permeable to the liquids that are intended to be held or stored by the absorbent article, and the backsheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface.

An absorbent article, such as a diaper, comprises a front waistband region, a back waistband region, an intermediate crotch region which interconnects the front and rear waistband regions. When used herein, reference to a "front" portion refers to that part of the absorbent article which is generally located on the front of a subject, such as an infant or adult, when in use. Reference to the "rear" portion refers to the portion of the absorbent article generally located at the rear of the subject, such as an infant or adult, when in use, and reference to the "crotch" portion refers to that portion which is generally located between the legs of subject, such as an infant or adult, when in use. The crotch region is an area where repeated fluid surge typically occurs, within the absorbent article assembly.

"Front", "rear or back", and "crotch" portions of the absorbent core as used herein typically refer to portions of the absorbent core that are proximal to respective portions of the absorbent article. For example, the "front" portion of the core is that which is most proximal to the front of the subject when worn, the "rear or back" portion of the core is that which is most proximal to the rear or back of the subject when worn, and the "crotch" portion of the core is the middle portion of the absorbent core between the "front" and "rear or back" portions.

The "absorbent medium" or "absorbent core" or "absorbent body" is the absorbent structure disposed between the topsheet and the backsheet of the absorbent article in at least the crotch region of the absorbent article and is capable of absorbing and retaining liquid body exudates. The size and the absorbent capacity of the absorbent medium should be compatible with the size of the intended wearer and the liquid loading imparted by the intended use of the absorbent article. Further, the size and the absorbent capacity of the absorbent medium can be varied to accommodate wearers ranging from infants through adults. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material.

"Acquisition distribution layer", "ADL" or "surge management portion" refers to a sub-layer which preferably is a nonwoven wicking layer arranged directly under the topsheet of an absorbent product, which speeds up the transport and improves distribution of fluids throughout the absorbent core. The surge management portion is typically less hydrophilic than the retention portion (described afterwards), and has the ability to quickly collect and temporarily hold liquid surges, and to transport the liquid from its initial entrance point to other parts of the absorbent structure, particularly the retention portion. This configuration can help prevent the liquid from pooling and collecting on the portion of the absorbent garment positioned against the wearer's skin, thereby reducing the feeling of wetness by the wearer. Preferably, the surge management portion is positioned between the topsheet and the retention portion.

The term "bulk density" as used herein refers to the weight of a material per unit of volume. Bulk density is generally expressed in units of weight/volume (e.g., grams per cubic centimeter, $g \cdot cm^{-3}$). The bulk density of flat, generally planar materials such as, for example, fibrous nonwoven webs, may be derived from measurements of thickness and basis weight of a sample. The thickness of the samples is determined utilizing a Model 49-70 thickness tester available from TMI (Testing Machines Incorporated) of Amityville, New York (alternatively, a portable thickness gauge J 100/A may be used). The thickness is measured using a 6.45 cm (2-inch) diameter circular foot at an applied pressure of about $1.38 \cdot 10^3$ Pa (about 0.2 pounds per square inch (psi)). The basis weight of the sample is determined essentially in accordance with ASTM D-3776-9 with the following changes: 1) sample size is cut to 10.16 cm×10.16 cm (4 inches×4 inches) square and 2); a total of 9 samples are weighed.

The term "specific volume" as used herein refers to the inverse bulk density of material being measured in volume per a unit weight and may be expressed in units of cubic centimeters per gram.

The term "mean flow pore size" as used herein refers to a measure of average pore diameter as determined by a liquid displacement technique such as using a Coulter Porometer and Coulter POROFIL® test liquid available from Coulter Electronics Limited, Luton, England. The mean flow pore size is determined by wetting a test sample with a liquid having a very low surface tension (i.e., Coulter POROFIL®). Air pressure is applied to one side of the sample. Eventually, as the air pressure is increased, the capillary attraction of the fluid in the largest pores is overcome, forcing the liquid out and allowing air to pass through the sample. With further increases in the air pressure, progressively smaller and smaller holes will clear. A flow versus pressure relationship for the wet sample can be established and compared to the results for the dry sample. The mean flow pore size is measured at the point where the curve representing 50% of the dry sample flow versus pressure intersects the curve representing wet sample flow versus pressure. The diameter of the pore which opens at that particular pressure (i.e., the mean flow pore size) can be determined from the following expression:

$$Pore\ Diameter\ (\mu m) = (40\tau)/pressure$$

where $\tau$=surface tension of the fluid expressed in units of mN/M; the pressure is the applied pressure expressed in millibars (mbar); and the very low surface tension of the liquid used to wet the sample allows one to assume that the contact angle of the liquid on the sample is about zero.

The term "adhesive" as used herein is intended to refer to any suitable hot melt, water or solvent borne adhesive that can be applied to a surface of a film layer in the required pattern or network of adhesive areas to form the film-nonwoven laminate of the present disclosure. Accordingly, suitable adhesives include conventional hot melt adhesives, pressure-sensitive adhesives and reactive adhesives (i.e., polyurethane).

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein, an "airlaid web" is a fibrous structure formed primarily by a process involving deposition of air-entrained fibers onto a mat, typically with binder fibers present, and typically followed by densification and thermal bonding. In addition to traditional thermally bonded airlaid structures (those formed with non-tacky binder material present and substantial thermally bonded), the scope of the term "airlaid" according to the present disclosure can also include coform, which is produced by combining air-entrained dry, dispersed cellulosic fibers with meltblown synthetic polymer fibers while the polymer fibers are still tacky.

As used herein, an "air-through bonded" nonwoven, is a nonwoven structure primarily formed by a process that comprises the application of heated air to the surface of the nonwoven fabric. Air-through bonding uses high temperature air to fuse the web's fibers. There may be two basic systems: blowing hot air through the web in a conveyor oven or passing heated air through the web on a rotating drum. During the through air bonding process, heated air may flow through holes in a plenum above the nonwoven material. Unlike hot ovens, which push air through the material, the through air process may use negative pressure of suction to pull the air through an open conveyor apron holding nonwoven as it is drawn through the oven. Pulling air through the material allows the rapid and even transmission of heat to minimize distortion of the nonwoven material. The binding agents used in the through air bonding process include crystalline binder fibers and powders, which melt to form molten droplets throughout the cross-section of the nonwoven. As the material is cooled, bonding occurs at these droplet points.

As used therein, the term "associated" encompasses configurations in which topsheet is directly joined to backsheet by affixing topsheet directly to backsheet, and configurations wherein topsheet is joined to backsheet by affixing topsheet to intermediate members which in turn are affixed to backsheet. Topsheet and backsheet can be affixed directly to each other by attachment means such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet to backsheet. It should be readily appreciated that the above-described attachment means may also be employed to interconnect and assemble together the various other component parts of the article described herein.

The term "backsheet" or "backsheet" refers to a material forming the outer cover of the absorbent article. The backsheet prevents the exudates contained in the absorbent structure from wetting articles such as bedsheets and overgarments which contact the disposable absorbent article. The backsheet may be a unitary layer of material or may be a composite layer composed of multiple components assembled side-by-side or laminated. The backsheet may be the same or different in different parts of the absorbent article. At least in the area of the absorbent medium the backsheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The backsheet material may be breathable so as to allow vapour to escape from the absorbent material, while still preventing liquids from passing there through. Examples of breathable backsheet materials are porous polymeric films, nonwoven laminates of spunbond and meltblown layers and laminates of porous polymeric films and nonwoven materials.

The term "blend" means a mixture of two or more polymers while the term "alloy" means a sub-class of blends wherein the components are immiscible but have been compatibilized.

As used herein, the "skin-facing", "body-facing" or "bodyside" surface means that surface of the article or component which is intended to be disposed toward or placed adjacent to the body of the wearer during ordinary use, while the "outward", "outward-facing" or "garment-side" surface is on the opposite side, and is intended to be disposed to face away from the wearer's body during ordinary use. Such outward surface may be arranged to face toward or placed adjacent to the wearer's undergarments when the absorbent article is worn.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

The term "breathable" refers to films having a water vapor transmission rate (WVTR) of at least 300 grams/m²-24 hours.

"Carded web (or layer(s) or nonwoven)" refers to webs that are made from staple fibers that are sent through a combing or carding unit, which opens and aligns the staple fibers in the machine direction to form a generally machine direction-oriented fibrous nonwoven web. The web is then bonded or consolidated by one or more of several known methods. Bonding or consolidation of nonwoven webs may be achieved by a number of methods: (i) powder bonding, wherein a powdered adhesive or a binder is distributed through the web and then activated, usually by heating the web and adhesive with hot air; (ii) pattern bonding, wherein heated calendar rolls or ultrasonic bonding equipment are used to bond the fibers together, usually in a localized bond pattern, though the web can be bonded across its entire surface if so desired (resulting nonwovens may be called (carded) thermobonded (because the bonding is achieved by use of heat), calender bonded, point bonded); (iii) through-air bonding, wherein air which is sufficiently hot to soften at least one component of the web is directed through the web (resulting nonwovens may be called (carded) through air or (carded) air-through—whilst the bonding is also achieved by use of heat, like in (carded) thermobonded, air through bonding differs in that it uses heated air); (iv) chemical bonding using, for example, latex adhesives that are deposited onto the web by, for example, spraying (powder bonding and chemical bonding may sometimes refer as adhesive bonding and resulting nonwovens may be called (carded) adhesive bonded, (carded) latex or resin bonded); and (v) by mechanical methods such as needling (resulting nonwovens may be called needlepunched) or with the use of water jets e.g. hydroentanglement (resulting nonwovens may be called spunlaced or hydroentangled).

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

"Chassis" refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Coform" as used herein is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent particles. The meltblown fibers containing wood fibers are collected on a forming surface, such as provided by a foraminous belt. The forming surface may include a gas-pervious material, such as spunbonded fabric material, that has been placed onto the forming surface.

"Compression" refers to the process or result of pressing by applying force on an object, thereby increasing the density of the object.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added e.g. to enhance processability of the composition.

The diaper can comprise "containment flaps" or "barrier cuffs". The containment flaps are generally thought to be particularly well suited for the containment of fecal matter and to prevent the lateral flow of liquid waste until such time as the liquid waste can be absorbed by the absorbent article. Many constructions of containment flaps are known. Such containment flaps generally comprise a proximal edge, intended to be attached to the absorbent article, and an opposite distal edge which is generally not attached to the absorbent article along at least a portion of its length. An elastic member is generally located adjacent the distal edge to assist in maintaining the containment flap in an upright condition and in maintaining a sealing relationship between the distal edge of the containment flap and the body of a wearer during use. The containment flaps may be manufactured from a wide variety of materials such as polypropylene, polyester, rayon, nylon, foams, plastic films, formed films, and elastic foams. A number of manufacturing techniques may be used to manufacture the containment flaps. For example, the containment flaps may be woven, nonwoven, spunbonded, carded, cast, blown or the like.

The diaper can comprise leg containment gaskets. Leg "containment gaskets" help prevent leakage of bodily exudates when the wearer exerts compressive forces on the absorbent article. In particular, the stiffness of the leg containment gaskets prevents twisting and bunching of the leg openings of the absorbent article which can lead to leaks. In addition, the elasticity and conformability of the leg containment gaskets ensures that the bodyfacing surface of the leg containment gaskets provides an adequate seal against the body of the wearer.

A "continuous waistband" can be an elastomeric, cloth-like, nonwoven fibrous material, such as an elastomeric stretch bonded laminate web or an elastomeric meltblown web.

The term "density" or "concentration" when referring to the absorbent material, in particular the SAP, of a layer, refers to the amount of the absorbent material divided by the surface area of the layer over which the absorbent material is spread out. The density can be measured using the same methodology as described previously for the bulk density.

The term "density" when referring to the topsheet or the acquisition distribution layer, refers to the weight of said layer divided by the volume of said layer and is expression in gram per cubic meter ($g \cdot m^{-3}$). The density can be measured using the same methodology as described previously for the bulk density.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the terms "elastic", "elastomeric", "elasticity" or derivations thereof are used to describe the ability of various materials and objects comprised of such to reversibly undergo deformation under stress, e.g., become stretched or extended, in at least one direction when a force is applied to the material and to resume substantially to their original dimensions upon relaxing, i.e., when the force is released, without rupture or breakage. Preferably, it refers to a material or composite which can be elongated in at least one direction by at least 50% of its relaxed length, i.e., elongated to at least 150% of its relaxed length, and which will recover upon release of the applied tension at least 40% of its elongation. Accordingly, upon release of the applied tension at 50% elongation, the material or composite contracts to a relaxed length of not more than 130% of its original length. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

The term "elasticized" refers to a material, layer, or substrate that is naturally non-elastic, but which has been rendered elastic by, for example, suitably joining an elastic material, layer, or substrate thereto.

"Elongation" means the ratio of the extension of a material to the length of the material prior to the extension (expressed in percent), as represented by the following:

"Extension" means the change in length of a material due to stretching (expressed in units of length). The term "extensible" means elongatable in at least one direction, but not necessarily recoverable.

The term "fabrics" is used to refer to all of the woven, knitted and nonwoven fibrous webs. "Fastening means", such as tape tab fasteners, are typically applied to the back waistband region of the diaper to provide a mechanism for holding the diaper on the wearer. Fastening means, such as tape tab fasteners, snaps, pins, belts, hooks, buckles, "hook/mushroom"-and-loop fasteners (e.g. VELCRO®-type fasteners) and the like, may be employed and are typically applied at the lateral, side ends of the back waistband region of diaper to provide a mechanism for holding the diaper about the waist of the wearer in a conventional manner. Tape tab fasteners can be any of those well known in the art, and are typically applied to the corners of the diaper. For example, adhesive fasteners, mechanical fasteners, hook-and-loop fasteners, snaps, pins or buckles, may be used alone, or in combination. For example, the fasteners can be adhesive fasteners, which are constructed to releasably adhere to a landing zone patch attached to the front waistband section of the diaper to provide a refastenable adhesive fastening system.

The term "finished" or "final", when used with reference to a product, means that the product has been suitably manufactured for its intended purpose.

As used herein, the term "garment" means any type of apparel which may be worn. This includes diapers, training pants, incontinence products, surgical gowns, industrial workwear and coveralls, undergarments, pants, shirts, jackets and the like.

Many of the known superabsorbent polymer particles exhibit gel blocking. "Gel blocking" occurs when superabsorbent polymer particles are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of SAP in the absorbent member are even close to being fully saturated or before the fluid can diffuse or wick past the "blocking" particles into the rest of the absorbent member. Gel blocking can be a particularly acute problem if the superabsorbent polymer particles do not have adequate gel strength and deform or spread under stress once the particles swell with absorbed fluid.

The term "graphic" includes, but is not limited to, any type of design, image, mark, figure, codes, words, patterns, or the like. For a product such as a training pant, graphics will generally include objects associated with little boys and little girls, such as multi-color trucks, airplanes, balls, dolls, bows, or the like.

"Hydroentanglement process" refers to the manufacturing of nonwoven webs. The process involves directing a series of water jets towards a fibrous web which is supported on a moving porous belt. The water jets pass downwards through the mass of fibres and on making contact with the surface of the belt, the jets rebound, and break up: the energy released causes entanglement of the mass of fibres.

The term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. The term "wettable" is meant to refer to a fiber which exhibits a liquid, such as water, synthetic urine, or a 0.9 weight percent aqueous saline solution, in air contact angle of less than 90°, whereas "hydrophobic" or "non-wettable" describes fibers having contact angles equal to or greater than 90°.

As used herein, the term "impermeable" generally refers to articles and/or elements that are substantially not penetrated by aqueous fluid through the entire thickness thereof under a pressure of 1.0 kPa or less. Preferably, the impermeable article or element is not penetrated by aqueous fluid under pressures of 3.4 kPa or less. More preferably, the impermeable article or element is not penetrated by fluid under pressures of 6.8 kPa or less. An article or element that is not impermeable is permeable.

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

"Laminate" refers to elements being attached together in a layered arrangement.

The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like. When used in the singular, it can have the dual meaning of a single element or a plurality of elements.

The crotch portion of the absorbent article preferably comprises opposite longitudinal side portions which comprise a pair of elasticized, longitudinally-extending "leg cuffs". The leg cuffs are generally adapted to fit about the legs of a wearer when in use and serve as a mechanical barrier to the lateral flow of body exudates. Leg cuffs are elasticized by leg elastics. Exemplary of such materials are strands or ribbons of a polymeric, elastomeric material which are adhered to the diaper at the leg cuff while in a stretched position, or which are attached to the diaper while the diaper is pleated, such that elastic constrictive forces are imparted to the leg cuff. Examples of suitable elastomer materials that can be used include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

"Liquid" means a nongaseous substance and/or material that flows and can assume the interior shape of a container into which it is poured or placed.

The term "meltblown fibers" means fibers formed by extruding a molten thermoplastic material through a plurality of fine, usually circular, die capillaries as molten threads or filaments into a high velocity gas stream (e.g. air) which attenuates the filaments of molten thermoplastic material to reduce their diameter, which may be to microfiber diameter. In general, meltblown fibers have an average fiber diameter of up to about 10 microns. After the fibers are formed, the meltblown fibers are carried by the high velocity gas stream and are deposited on a collecting surface to form a web of randomly disbursed meltblown fibers.

The term "nonwoven fabric", "nonwoven layer" or "nonwoven web" means a sheet material having a structure of individual fibers or threads which are interlaid, but not in a regular manner such as occurs with knitting or weaving processes. Nonwoven fabrics, layer or webs have been formed from many processes such as for example, meltblowing processes, spunbonding processes, and bonded carded web processes.

By the terms "particle", "particles", "particulate", "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

The term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

"Pulp fluff" or "fluff pulp" refers to a material made up of cellulose fibers. The fibers can be either natural or synthetic, or a combination thereof. The material is typically lightweight and has absorbent properties.

As used herein the term "sheet" or "sheet material" refers to woven materials, nonwoven webs, polymeric films, polymeric scrim-like materials, and polymeric foam sheeting.

The absorbent article may also contain side panels. The "side panels" can have any shape such as but not limited to square, rectangular, triangular, circular and trapezoidal shape. They can be joined to the respective opposite side portions of the back section, by a known method, such as heat-sealing or adhesive bonding. Preferably, the side panels are formed by laminating a layer of nonwoven fabric, a layer of thermoplastic film and a layer of elastic material. The layer of elastic material might be sandwiched between the nonwoven fabric layer and the thermoplastic film by adhesive layers. The layer of nonwoven fabric might be made of natural fibers, synthetic fibers or a blend of natural fibers and synthetic fibers. The layer of thermoplastic film might be made of polyethylene or polypropylene.

The term "spunbond or spunbonded fibers (or layer(s) or nonwovens)" refers to fibers formed by extruding molten thermoplastic polymers as filaments or fibers from a plurality of relatively fine, usually circular, capillaries of a spinneret, and then rapidly drawing the extruded filaments by an eductive or other well-known drawing mechanism to impart molecular orientation and physical strength to the filaments. The average diameter of spunbond fibers is typically in the range of from 15-60 µm or higher. The spinneret can either be a large spinneret having several thousand holes per meter of width or be banks of smaller spinnerets, for example, containing as few as 40 holes. Spunbond or spunbonded is a spunlaid technology in which the filaments have been extruded, drawn and laid on a moving screen to form a web. The industry has conventionally adopted the spunbond or spunbonded term to denote a specific web forming process including calender bonding. This is to differentiate this web forming process from other forms of the spunlaid web forming, e.g. melt blown and flashspinning.

The term "spunbond meltblown spunbond" (SMS) nonwoven fabric as used herein refers to a multi-layer composite sheet comprising a web of meltblown fibers sandwiched between and bonded to two spunbond layers. A SMS nonwoven fabric can be formed in-line by sequentially depositing a first layer of spunbond fibers, a layer of meltblown fibers, and a second layer of spunbond fibers on a moving porous collecting surface. The assembled layers can be bonded by passing them through a nip formed between two rolls that can be heated or unheated and smooth or patterned. Alternately, the individual spunbond and meltblown layers can be pre-formed and optionally bonded and collected individually such as by winding the fabrics on wind-up rolls. The individual layers can be assembled by layering at a later time and bonded together to form a SMS nonwoven fabric. Additional spunbond and/or meltblown layers can be incorporated in the SMS fabric, for example spunbond-meltblown-meltblown-spunbond (SMMS), or spunbond-meltblown (SM) etc.

"Staple fibers" refer to commercially available fibers having diameters ranging from less than about 0.001 mm to more than about 0.2 mm; they come in several different forms such as short fibers ranging from about 10 to 50 mm in length and long fibers with a length higher than 50 mm, preferably up to 100 mm.

By "stretch", it is meant that the material has the ability to extend beyond its original size in at least one dimension when subjected to a tensile force (i.e., tension) applied in the direction of that dimension, without breaking the material. Stretch may be unidirectional, bi-directional, or multi-directional. The term can include elastic materials, as well as nonwovens that can be inherently extensible, but not necessarily in an elastic manner. Such nonwovens can be made to behave in an elastic manner by bonding them to elastic films.

By "channels", it is meant that the structure referred to (e.g. the absorbent core) comprises recessed regions forming visible conduits or passages typically extending along the longitudinal axis of the core and having a depth in a direction perpendicular to said longitudinal axis. By "visible" it is herein intended clearly visible by naked eye and typically that the channels have a width generally greater than 1 mm, preferably from 5 mm to 50 mm, more preferably from 8 mm to 40 mm, more preferably from 10 mm to 30 mm, even more preferably from greater than 10 mm to less than 25 mm.

By "interconnected", it is meant that the structure referred to (e.g. the channels) forms a substantially continuous path such as from a first end of a channel to a second end of the same channel.

By "substantially", it is meant at least the majority of the structure referred to. For example, with reference to interconnected channels, "substantially interconnected" means that the majority of the channel is interconnected and generally wherein a direct and continuous path can be traced by starting from one end of the channel towards another end of the channel, said ends (also referred to herein as terminal positions) being distal to each other in a width direction of the core and proximal to a portion of the perimeter of the core, preferably the sides thereof.

By "directly over", it is meant that the feature referred to is placed over the structure referred to such that the two are in direct contact with each other at least throughout a substantial portion of said structure.

By "indirectly over", it is meant that the feature referred to is placed over the structure referred to but in such a way that the two are not in direct contact with each other at least throughout a substantial portion of said structure. For example, a nonwoven web applied indirectly over a three-dimensional absorbent material comprises a further layer of material between said nonwoven web and said three-dimensional absorbent material.

Use of the term "substrate" includes, but is not limited to, woven or nonwoven webs, porous films, ink permeable films, paper, composite structures, or the like.

Superabsorbent materials suitable for use in the present disclosure are known to those skilled in the art, and may be in any operative form, such as particulate form, fibers and mixtures thereof. Generally stated, the "superabsorbent material" can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 µm, preferably between 300 to 600 µm, more preferably between 400 to 500 µm.

"Tension" includes a uniaxial force tending to cause the extension of a body or the balancing force within that body resisting the extension.

As used herein, the term "thermoplastic" is meant to describe a material that softens when exposed to heat and which substantially returns to its original condition when cooled to room temperature.

The term "topsheet" refers to a liquid permeable material sheet forming the inner cover of the absorbent article and which in use is placed in direct contact with the skin of the wearer. The topsheet is typically employed to help isolate the wearer's skin from liquids held in the absorbent structure. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. The topsheet material may further be composed of two fibres, which may be bonded to each other in a bonding pattern. The topsheet fabrics may be composed of a substantially hydrophobic material, and the hydrophobic material may optionally be treated with a surfactant or otherwise processed to impart a desired level of wettability and hydrophilicity.

"Ultrasonic welding" refers to a technology which joins two materials by melting them with heat generated from ultrasonic oscillation and then laminating them together, such that the molten materials flow and fill the gap between the two unaffected portions of the two materials, respectively. Upon cooling and shaping, the two materials are joined together.

"Dry-state" refers to the condition in which an absorbent article has not yet been saturated with exudates and/or liquid.

"Wet-state" refers to the condition in which an absorbent article has been saturated with exudates and/or liquid. Typically wherein at least 30 ml, preferably at least 40 ml, even more preferably at least 50 ml, most preferably from 60 ml to 800 ml, of exudate and/or liquid are contained in the absorbent article.

By the term "concentration" of (e.g. super absorbent polymer) as used herein, is meant the amount of the referred material divided by the surface area of the layer referred to (typically said area being in the plane of the length and width of the core) over or within which the referred material is contained. This may be determined by standard weighing and dimensional measuring methods known in the art and can be expressed in $g/mm^2$.

By the term "substantially U-shaped" as used herein, is meant any shape that visually approximates the shape of a "U", such as a "V-shape", a semi-circle, and the like.

By the term "distinct cellulosic fibers" as used herein, is meant cellulosic fibers that are not part of a substrate (e.g. a nonwoven layer) and are rather distinct thereof and/or physically separated therefrom, and typically are in the form of cellulosic fibers that are enclosed though kept separate from said substrate. For sake of clarity, cellulosic fibers present within a substrate (e.g. a nonwoven layer) are not encompassed within its meaning.

By the term "substantially follows the shape of the channel(s)" as used herein, is meant that the feature referred to has an overlapping shape that is visually the same as the channel(s).

Embodiments according to the disclosure will now be described. It is understood that technical features described in one or more embodiments maybe combined with one or more other embodiments without departing from the intention of the disclosure and without generalization therefrom.

Absorbent Article

As illustrated in FIG. 1, the absorbent article 10 according to the present disclosure comprises an absorbent core 12 arranged between a liquid permeable topsheet 14 and a liquid impermeable backsheet 16. An acquisition distribution layer 18 is positioned between said topsheet 14 and said absorbent core 12. The absorbent core 12 comprises absorbent material 20 selected from the group consisting of cellulose fibers 22, superabsorbent polymers 24 or a combination thereof. The absorbent core 12 comprises at least one channel 26 substantially free of cellulose fibers 22 and/or substantially free of superabsorbent polymer 24. As illustrated in FIG. 1, the absorbent core 12 comprises two channels 26, or one single channel 26 that is interconnected.

The topsheet 14 is associated to the backsheet 16. The topsheet 14 can be directly joined to backsheet 16 by affixing the topsheet 14 directly to the backsheet 16. Alternatively, the topsheet 14 can be indirectly joined to the backsheet 16 by affixing the topsheet 14 to intermediate members which in turn are affixed to the backsheet 16. Topsheet layer 14 and backsheet 16 can be affixed directly to each other or to intermediate members by attachment means such as an adhesive, sonic bonds, thermal bonds or any other attachment means known in the art. The absorbent article 10 can also comprise a topsheet 14 that has a portion directly joined to the backsheet 16 and another portion indirectly joined to the backsheet 16.

According to an embodiment, the backsheet 16 comprises a print or graphic viewable from the garment facing side of said article that substantially matches the shape and/or contour of the channel(s) 26. This embodiment having the advantage to further accentuate the visual perception of the presence of such channel and its location in the absorbent article.

In an embodiment, the absorbent article comprises a topsheet 14 and a backsheet 16 directly or indirectly enclosing the core, wherein at least one of the backsheet 16 or topsheet 14 comprises a color that is different from the color of the core, preferably wherein the backsheet 16 has a color that is different from the color of the topsheet 14 and core, such that the channels may be visually discernible from the topsheet 14 side of the article Acquisition Distribution Layer 18

One particular component used in absorbent articles 10 herein is an acquisition distribution layer 18, also commonly called ADL. The ADL 18 may be positioned at a body-facing side of the absorbent core 12, between the topsheet 14 and the absorbent core 12 of the absorbent article, and more preferably in close proximity or even in good contact with the body-facing side of the absorbent core 12. The use of an ADL 18 in combination with the at least one channel 26 leads to an extremely good distribution of fluids from a discharge area to the entire absorbent core 12 whilst attaining excellent perceived dryness performance.

According to the invention, the acquisition distribution layer 18 for use herein comprises, consists essentially of, or consists of, a spunbond and/or thermocarded, i.e a carded thermobonded, nonwoven layer. Such nonwoven layer enables to have a compact dense layer, thereby improving the size of the absorbent article as well as improving the wicking effect as it will be described later on.

In an embodiment, the acquisition distribution layer 18 comprises, consists essentially of, or consists of, a, preferably single, spunbonded or thermocarded nonwoven layer and is free of air-through bonded, airlaid and/or spunlaced nonwoven layers. Indeed, a spunbonded or thermocarded nonwoven layer, even more if single, will result in a compact and dense ADL as opposed to an air-though bonded, airlaid and/or spunlaced nonwoven layer. We have found that an air-though bonded nonwoven as ADL in the present configuration was too bulky, lofty and porous and was slowing down the dewatering effect of the ADL on liquid stool. A spunlaced nonwoven layer may also not be convenient as ADL in the present configuration, because of a non-homogeneous density showing well a dense material but also inconvenient big holes, and because it is generally a high weight material.

In an embodiment the spunbonded layer of the ADL is part of a multi-layer composite sheet additionally comprising a web of meltblown fibers. In particular the spunbonded layer of the ADL may be a SM, SMS or SMMS multi-layer composite sheet.

According to an embodiment, the spunbonded and/or thermocarded nonwoven layer may comprise synthetic fibers that are comprised at a level of greater than 80% by weight of said acquisition distribution layer 18.

According to an embodiment, the acquisition distribution layer 18 has a basis weight of from 10 to 50 g/m$^2$, preferably from 15 to 40 g/m$^2$, more preferably from 18 to 35 g/m$^2$, even more preferably from 20 to 32 g/m$^2$.

According to an embodiment, the acquisition distribution layer 18 has a specific volume of less than 11.4 cm$^3$/g, preferably less than 11.3 cm$^3$/g, more preferably from 5.5 cm$^3$/g to 11.2 cm$^3$/g, even more preferably from 8.5 cm$^3$/g to 11.17 cm$^3$/g. Advantageously, a specific volume within these ranges allows to limit sponge-like rewet drawbacks whilst still ensuring fast acquisition speeds when combined with channeled cores as described herein.

According to an embodiment, the synthetic fibers are comprised at a level of greater than 90% wt, preferably from 95% to 100% by weight of said acquisition distribution layer 18.

According to an embodiment, the acquisition distribution layer 18 consists essentially of synthetic fibers and is preferably free of cellulose fibers. The acquisition distribution layer 18 may be treated, such as with a surfactant, to render said layer 18 hydrophilic. Preferably, the synthetic fibers comprise, preferably consist of polypropylene, polyethylene or polyester such as polyethylene terephthalate fibers or a combination thereof. Perceived dryness is improved by further eliminating cellulose fibers from the ADL.

Preferably, the acquisition distribution layer 18 has a mean flow pore size of from 15 μm to 200 μm, preferably from 30 μm to 150 μm, more preferably from 45 μm to 130 μm, even more preferably from 55 μm to 110 μm, even more preferably from 60 μm to less than 100 μm, even more preferably from 65 μm to 95 μm, even more preferably from 70 μm to 90 μm. Without wishing to be bound by theory, if the pore size is too small the nonwoven will retain more liquid therein and have reduced liquid-flush-out performance, on the other hand if the pore size is too large the nonwoven will not have the desirable wicking properties to still provide acceptable liquid distribution across the core.

Preferably, the acquisition distribution layer 18 has a relative porosity, or air permeability, of from 1 000 L/m$^2$/s to 7 000 L/m$^2$/s, preferably of from 1 500 L/m$^2$/s to 6000 L/m$^2$/s, preferably from 2000 L/m$^2$/s to 5000 L/m$^2$/s, more preferably from 3000 L/m$^2$/s to 5000 L/m$^2$/s, most preferably from 3500 L/m$^2$/s to 4500 L/m$^2$/s. Advantageously, nonwovens having relative porosity within these ranges allow for a reduced sponge-like behavior whilst providing good liquid distribution performance.

Absorbent Core 12

The absorbent core 12 according to the present disclosure may comprise: a front portion 122; a back portion 124; a middle portion 126 positioned between the front portion 122 and the back portion 124; and extends in a longitudinal direction 48 along a length of said absorbent core 12 and crossing said front, middle and back portions 122, 126, 124, the absorbent core 12 extends in a transversal direction 49 along a width of said absorbent core 12, said with being perpendicular to said length and a perimeter comprising at least two opposing longitudinal ends, or edges, 102, 103 and at least two opposing transversal sides 104, 105 positioned between said ends 102, 103.

Figure 3:
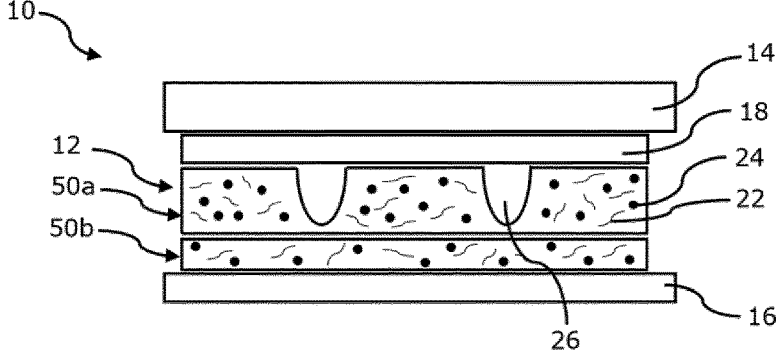
FIG. 3 illustrates a diagrammatic cross section of an absorbent article according to an embodiment.

The absorbent core 12 can comprise a single layer, as illustrated in FIG. 1, or a plurality of layers as exemplified in FIG. 3.

In the embodiment illustrated in FIG. 3, the absorbent core 12 comprises at least two distinct core layers 50a,50b, wherein a first core layer 50a comprises a first concentration of super absorbent polymer 24a therein and a second core layer 50b comprises a second concentration of super absorbent polymer 24b therein said first and second concentrations being different. Preferably, the second concentration of super absorbent polymer is greater than the first concentration of super absorbent polymer, preferably wherein said second concentration is at least 1.5, preferably 2, times greater than the first concentration. Such brings advantages such as reduced risk of gel-blocking.

The single layer of the absorbent core 12 (FIG. 1) or the first absorbent core layer 50a (FIG. 3) comprises one or more channels 26, said channel(s) 26 being continuous and interconnected at least along the length and the width of said absorbent core 12 such that at least two channel portions 107,108 extending along said length are in fluid communication via a connecting channel portion 109 positioned proximal to said back portion 124. An advantage of this arrangement is that a synergistic and efficient fluid distribution and absorption is achieved within the core, with the channel shape providing immediate fluid re-distribution along the core length and width especially from the front to the back of the article, and the multi-layered core arrangement with differential superabsorbent polymer concentration enables to more efficiently absorb said fluids in a multi-fold way and reduce the risk of gel-blocking.

Preferably, the channel(s) 26 herein do not extend up to any of the edges 102, 103, 104, 105 forming the perimeter of the absorbent core 12.

Preferably, the connecting channel portion 109 forms a substantially U-shaped bend, preferably wherein the single layer of the absorbent core 12 or first core layer 50a comprises a single channel 26. Such shape optimizes the fluid distribution properties of the core.

Preferably, the channel(s) 26 comprises a single connecting channel portion 109, such that a continuous superabsorbent polymer area (typically in the core length/width plane) is formed around said channel(s) and generally no superabsorbent polymer area is fully enclosed by portions of said channel(s) 26. This arrangement allows for optimal fluid distribution with limited risk of forming over and under saturated areas in the core, as well as reducing the risk of delamination of layers joined together forming the channel(s).

Preferably, at least one of the interconnected channels 26, preferably each said channel 26, forms a shape having an open end in the form of two diverging ends or a funnel-shape and a closed end opposite thereto formed by the connecting channel portion 109, preferably wherein the open end is positioned proximal to the front portion 122 of the absorbent core 101 and distal from said closed end. Advantages include promoted fluid distribution from front to back of the article.

According to an embodiment, the absorbent core 12 comprises at least one core wrap substrate enclosing the superabsorbent polymer therebetween. The core wrap can encapsulate the single layer 12, only one of the two layers or both of the layers 50a,50b. The core wrap can comprise a top core wrap and a bottom core wrap. The top layer of the core wrap is adhered to a bottom layer of the core wrap in regions of said core comprising the channel(s) 26 preferably such that substantially no (i.e. less than 1% wt, preferably less than 0.5% wt, more preferably less than 0.1% wt, even more preferably less than 0.05% wt, most preferably about 0% wt, by weight of the core wrap substrate) superabsorbent polymer 24 is present in said channel(s) 26. Such ensures that fluids can quickly flow along the channel direction without swelling/absorption slowing its path. The core wrap can comprise a thin layer of SMS nonwoven fabric.

The second core layer 50*b* can be core wrap free and comprises a single nonwoven carrier layer with immobilized superabsorbent polymer thereon or therein, wherein the nonwoven carrier layer is porous and the superabsorbent polymer is in the form of particles and immobilized by means of mechanical action, such as ultrasound; one or more adhesives; and combinations thereof. This arrangement has been found beneficial to reduce further bulkiness and raw materials of the core. Particularly by locking particles within the substrate, by e.g. ultrasound, such immobilization can be achieved without chemical adhesive treatments and thus consequently also reducing the risk of chemical contamination and/or need for multiple/additional layers to enclose said particles.

In an embodiment the interconnected channel 26 comprises a U-bend proximal to a back end of the absorbent article and first/second terminal ends 110, 111 proximal to the front of the absorbent article, generally when in dry state, and when in wet state (i.e. upon saturation with exudates and/or liquid) the channel is separated into a plurality (preferably two) distinct channels 26 and typically wherein said distinct channels 26 are free of said U-bend.

In an embodiment, the absorbent core 12 comprises at least one core wrap substrate enclosing one or more absorbent materials therein, preferably said absorbent material being selected from the group consisting of super absorbent polymers, cellulosic fibers, and combinations thereof, and wherein a top layer of the core wrap is adhered to a bottom layer of the core wrap to form an interconnected absorbent material-free channel(s) 26 (generally in dry state). Typically, regions where top and bottom layers are not bonded comprise absorbent material therebetween (generally separating the top layer from the bottom layer) and regions where the top and bottom layers are bonded together are substantially free of absorbent material to form channels within the absorbent material of the absorbent core. Preferably, the adhered top and bottom layers of the core wrap have a first bond in at least two distinct regions of the channel(s) 26 and a second bond in at least one other region of the channel(s) 26 connecting said at least two distinct regions, and wherein said second bond is arranged to break upon liquid saturation and/or expansion of the absorbent material whilst the first bond is arranged to remain intact upon liquid saturation and/or expansion of the absorbent material, preferably wherein said other region is the U-bend of the channel(s). More preferably the channel being arranged such that when in dry state one or more, preferably a single, interconnected channel 26 is visible and when in wet state a plurality of, preferably two, distinct channels 26 are visible. It is however evident that a core wrap (although preferred) is not necessary to achieve this effect, and rather other means could be envisioned such as by bonding in a similar manner a topsheet directly or indirectly to a backsheet without the need of a core wrap (thus the same features described above may be present/replaced by a topsheet/backsheet instead of the core wrap).

The first and second bonds may comprise a first and second adhesive respectively. The first and second adhesives being different, for example the second adhesive is selected to be soluble when in contact with liquid at body temperature (about 37° C.), such as pressure sensitive hotmelt adhesives having low melting point (i.e. a melting point of about 40° C.). The first adhesive may be selected from hotmelt adhesives that retain adhesive strength also upon contact with liquid at body temperature (i.e. have a melting point of more than 60° C., preferably more than 70° C., even more preferably more than 90° C.). In the above arrangement the second adhesive may be applied in the U-bend region whilst the first adhesive may be applied in all other regions of the channel.

In an alternative embodiment to the above, the same adhesive may be used throughout the channel, but in regions that should be released in wet-state, a lower pressure is applied between substrates when providing a joining force. For example, the pressure applied on the U-bend may be less (preferably less than half) than the pressure applied to all other regions of the channel.

Although, the above two are examples of how to achieve different channel shapes in Dry/Wet-state, other means for achieving the inventive arrangement may be considered and thus the application should not be so limited, for example the first and second bonds may provide a first and second bonding strength respectively, wherein the first bonding strength is greater than the second bonding strength. The bonding strength as used herein is preferably determined herein as the "peel strength".

Typically the first bond has a peel strength of greater than 5 g/mm, preferably more than 6 g/mm, even more preferably from 7 g/mm to 50 g/mm, and the second bond has a peel strength of less than 5 g/mm, preferably from 0.1 g/mm to 4 g/mm, more preferably from 0.2 g/mm to 3.5 g/mm, even more preferably from 0.3 g/mm to 3 g/mm, wherein the peel strength is generally determined according to ASTM Designation: D1876-72, "Standard Test Methods for Peel Resistance of Adhesives (T-Peel Test)", which is incorporated herein by reference.

In an embodiment the one or more interconnected channels are shaped such to effectively conduct fluid away from a region of discharge, typically by forming a shape that has a distance gradient between opposing surfaces of the interconnected channels, preferably forming a funnel-shaped profile.

In an embodiment, the channels form a geometric shape across the absorbent core and along a plane extending parallel to the longitudinal axis of said core, said geometric shape being selected from the group consisting of a semi-hourglass-shaped, v-shaped, u-shaped, pie-shaped, and combinations thereof. Wherein "by semi-hourglass-shaped" it is intended an hourglass shape with only a single end.

In an embodiment, the channels comprise, preferably consist of, a first nonwoven web bonded to a second nonwoven web by one or more adhesives. Preferably, the adhesive is applied in zones across the width of the channels such to form zones, preferably alternating zones, of different bonding strength between the nonwoven web laminate. For example the first nonwoven web may be bonded to the second nonwoven web on at least three zones along the width of the channel. Such arrangement may comprise a first adhesive zone, a second adhesive zone and a third adhesive zone, the second adhesive zone being interposed between the first and third adhesive zones along the width of the channel (e.g. at an axis parallel to the core width and perpendicular to the longitudinal axis of the core) wherein the bonding strength of the second adhesive zone is greater than the bonding strength of the first and third adhesive zones. Examples of ways to achieve such stronger bonding strength in the second zone include using higher amounts of adhesive in this zone, applying greater mechanical pressure on this zone, or utilizing a different adhesive type, other ways are also contemplated provided a stronger adhesion between nonwoven webs results in such region.

Hereby, connecting channel portion 109 of at least one of the interconnected channels, the connecting channel portion being in fluid communication with said first and second channel portions 107, 108, preferably forms said closed end in the form of a U-bend, preferably wherein the first and second channel portions 107, 108 diverge away from the longitudinal axis at least along a portion of the interconnecting channel 26 typically exiting from the U-bend, thereby at least partially forming a funnel-shaped interconnected channel near the closed end.

The first and second channel portions may be substantially linear; or have a substantially curved profile preferably selected from concave or convex; or may comprise a combination of said linear and curved profiles. In a preferred embodiment, the first and second channel portions are concave in shape and are generally symmetric about at least the longitudinal axis.

The first and second channel portions may extend through at least a majority, preferably the entirety, of the length of the crotch portion along the longitudinal axis and typically run substantially parallel to the sides of the core forming the perimeter thereof.

In a preferred embodiment, each interconnected channel herein comprises only a single connecting channel portion 109, typically forming an apex of the inter connected channel. An advantage of this embodiment is fast fluid distribution through the core whilst limiting the risk of blockages that could otherwise result if pockets of wetted areas are rather formed.

In an embodiment, the absorbent core 12 further comprises one or more disconnected channels, preferably at least a portion thereof being arranged concentrically to the substantially interconnected channel. An advantage being effective added local uniform fluid distribution. Moreover, it is believed that upon swelling of the neighboring regions to the channels, upon saturation, visual patterns may be formed that more evidently convey the perception of efficacy of the entire core surface for absorption of fluid.

Figure 2:
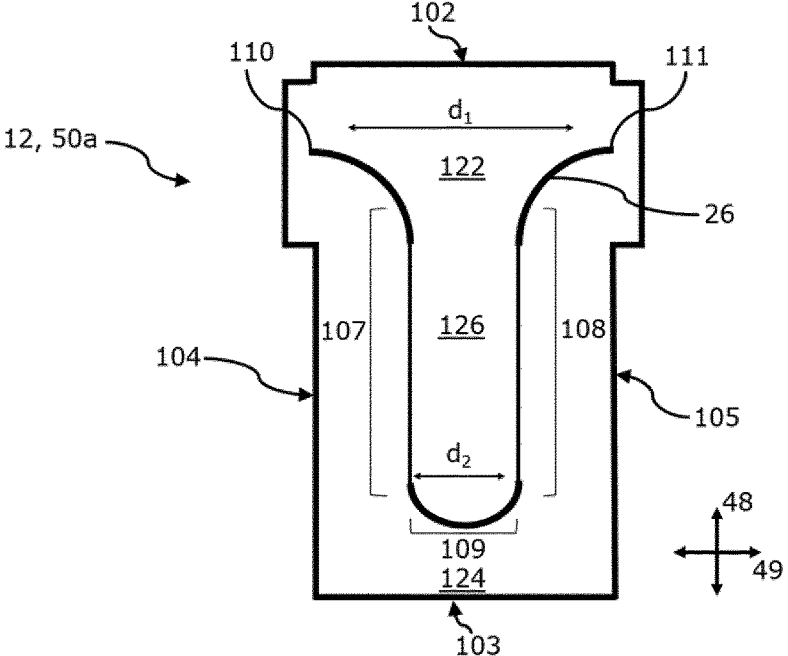
FIG. 2 shows a diagrammatic top view of an absorbent core according to an embodiment

In the embodiment, as illustrated in FIG. 2, the width of the interconnected channel 26 may vary along the channel. Preferably, the width of the channel decreases from the terminal positions 110, 111 towards the connecting channel portion 109. The width of the channel 26 near the first terminal position 110 and the width of the channel 26 near the second terminal position 111 are larger than the width of the channel 26 in the first channel portion 107 and the width of the channel 26 in the second channel portion 108, which are larger than the width of the channel 26 in the connecting channel portion 109. In the embodiment illustrated in FIG. 2, the width of the connecting channel portion 109 is larger than the first and/or second channel portion 107, 108. Such variance of the width of the channel portions leads to faster distribution. Without wishing to be bound by theory, the inventors believe that the varying width leverages capillary effects that better promote liquid transport from the front to the back of the absorbent article.

It is understood that a number of alternative shapes may be used for channels described herein without departing from the disclosure embodiments described herein The present disclosure further relates to an absorbent core comprising substantially continuous zones of one or more high fluid distribution structures and continuous or discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures and wherein said continuous zones extend along a path that is substantially parallel to at least a portion of the perimeter of the core, said portion of the perimeter of the core comprising at least a portion of the sides, preferably at least a portion of both of the sides of the core and one of the ends of the core (preferably only one end), preferably the end proximal to the back portion. Advantages of this embodiment includes separating absorbent regions of the core with fluid distribution regions that effectively uniformly distribute fluid across the core surface with a mechanism as described above as well as providing a visual perception of efficacy.

Topsheet 14

According to the invention, the absorbent article 10 comprises a liquid permeable topsheet 14 that is arranged on the body-facing side of the absorbent article 10. The topsheet 14 covers the ADL 18, so that the ADL 18 is sandwiched, preferably directly, between the absorbent core 12 and the topsheet 14. In other words, the topsheet 14 is positioned in close proximity, or even in good contact with the body-facing side of the ADL 18.

The topsheet 14 for use herein consists essentially of an air-through bonded nonwoven layer and is free of spunbond nonwoven layers.

In an embodiment, the topsheet 14 consists essentially of, or consists of, a, preferably single, air-through bonded nonwoven layer and is free of spunbond, carded, airlaid and/or meltblown nonwoven layers. Preferably the air-through bonded nonwoven layer is the most exterior layer of the body-facing side of the absorbent article, adapted to be in contact with the skin when the absorbent article is worn.

According to an embodiment, the air-through bonded nonwoven topsheet 14 may comprise synthetic fibers that are comprised at a level of greater than 80% by weight of said topsheet 18. For example, the synthetic fibers are comprised at a level of greater than 90% wt, preferably from 95% to 100% by weight of said topsheet 14.

According to an embodiment, the topsheet 14 has a basis weight of from 10 to 50 $g/m^2$, preferably from 20 to 40 $g/m^2$, more preferably from 25 to 35 $g/m^2$.

According to an embodiment, the topsheet 14 consists essentially of synthetic fibers and is preferably free of cellulose fibers. The topsheet 14 may be treated, such as with a surfactant, to render said topsheet 14 hydrophilic. Preferably, the synthetic fibers comprise, preferably consist of, polypropylene (PP), polyethylene (PE) or polyester such as polyethylene terephthalate (PET) fibers or a combination thereof. For example, the air-through bonded nonwoven layer, meaning the topsheet 14, comprises PP/PE bicomponent fibers, the topsheet 14 can also comprise PE/PET bicomponent fibers.

Preferably, the topsheet 14 has a mean flow pore size that is greater than the mean flow pore size of the acquisition distribution layer 18. Without wishing to be bound by theory, the mean flow pore size of the topsheet 14 is preferably greater than the mean flow pore size of the acquisition distribution layer 18 in order to reach the desired wicking properties of the absorbent article 10. In a analogous manner, the mean flow pore size of the acquisition distribution layer 18 is preferably greater than the mean flow pore size of the absorbent core 12 to further improve the wicking effect.

In other words, the mean flow pore size of the topsheet 14 is preferably greater than the mean flow pore size of the acquisition distribution layer 18 and the mean flow pore size of the acquisition distribution layer 18 is preferably greater than the mean flow pore size of the absorbent core 12.

Preferably, the topsheet 14 has an air permeability, or relative porosity, of from 4 000 $L/m^2/s$ to 12 000 $L/m^2/s$, preferably from 7 000 L/m²/s to 10 000 L/m²/s, more preferably from 8 500 L/m²/s to 9 500 L/m²/s. Without wishing to be bound by theory, the air permeability of the topsheet 14 is preferably greater than the air permeability of the acquisition distribution layer 18 in order to reach the desired wicking properties of the absorbent article. In an analogous manner, the air permeability of the acquisition distribution layer 18 is preferably greater than the air permeability of the absorbent core 12 to improve the wicking effect.

This improved capillary or wicking effect is improved by the nature of the different layers used herein. The topsheet 14 comprises an air-through bonded nonwoven layer, in other words, the topsheet 14 comprises a bulky, lofty and porous layer with higher air permeability. The acquisition distribution layer 18 comprises a spunbonded or thermocarded nonwoven layer, in other terms, the acquisition distribution layer 18 comprises a thin, compact with small pores and lower, or lesser, air permeability. Lastly, the absorbent core 12 comprises at least one cellulosic fluff pulp with superabsorbent polymers layer 50a,50b. The absorbent core 12 is even more compact and has smaller pores and a lesser, or lower, air permeability value than the ADL 18.

For example, as discussed above, the mean flow pore size of the topsheet 14 is preferably greater than the mean flow pore size of the acquisition distribution layer 18 and the mean flow pore size of the acquisition distribution layer 18 is preferably greater than the mean flow pore size of the absorbent core 12.

The synergetic combination of the absorbent core 12, acquisition distribution layer 18 and topsheet 14 as described above results in an absorbent structure comprising a gradient in air permeability where the top layer, the topsheet 14, has a greater air permeability than the acquisition distribution layer 18 and the acquisition distribution layer 18 has a greater air permeability than the absorbent core 12. The gradual decrease in air permeability results in an improved capillary or wicking effect without wishing to be bound by any theory.

For example, the air permeability of the topsheet 14 is of from 4 000 L/m²/s to 12 000 L/m²/s, preferably from 7 000 L/m²/s to 10 000 L/m²/s, more preferably from 8 500 L/m²/s to 9 500 L/m²/s. The air permeability of the ADL 18 is of from 1 000 L/m²/s to 7 000 L/m²/s, preferably of from 1 500 L/m²/s to 6 000 L/m²/s, preferably from 2 000 L/m²/s to 5 000 L/m²/s, more preferably from 3 000 L/m²/s to 5 000 L/m²/s, most preferably from 3 500 L/m²/s to 4 500 L/m²/s. The air permeability of the absorbent core 12 is of less than 1 000 L/m²/s, preferably of from 100 L/m²/s to 900 L/m²/s, preferably from 500 L/m²/s to 800 L/m²/s, more preferably from 600 L/m²/s to 700 L/m²/s.

As indicated by the examples, the air permeability of topsheet 14 can be 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9; 3; 3.1; 3.2; 3.3; 3.4; 3.5; 3.6; 3.7; 3.8; 3.9; 4; 4.1; 4.2; 4.3; 4.4; 4.5; 4.6; 4.7; 4.8; 4.9; 5; 5.1; 5.2; 5.3; 5.4; 5.5; 5.6; 5.7; 5.8; 5.9; 6; 6.1; 6.2; 6.3; 6.4; 6.5; 6.6; 6.7; 6.8; 6.9; 7; 7.1; 7.2; 7.3; 7.4; 7.5; 7.6; 7.7; 7.8; 7.9, 8; 9; 10; 11; 12 or more times greater than the air permeability of the acquisition distribution layer 18. In a analogous manner, the air permeability of acquisition distribution layer 18 can be 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9; 3; 3.1; 3.2; 3.3; 3.4; 3.5; 3.6; 3.7; 3.8; 3.9; 4; 4.1; 4.2; 4.3; 4.4; 4.5; 4.6; 4.7; 4.8; 4.9; 5; 5.1; 5.2; 5.3; 5.4; 5.5; 5.6; 5.7; 5.8; 5.9; 6; 6.1; 6.2; 6.3; 6.4; 6.5; 6.6; 6.7; 6.8; 6.9; 7 or more times greater than the air permeability of the absorbent core 12.

In other terms, the relative porosity, or air permeability, of the topsheet 14 is greater than the relative porosity, or air permeability, of the acquisition distribution layer 18 and the relative porosity, or air permeability, of the acquisition distribution layer 18 is greater than the relative porosity, or air permeability, of the absorbent core 12.

In parallel, the density of the topsheet 14 is lesser than the density of the acquisition distribution layer 18 and the density of the acquisition distribution layer 18 is lesser than the density of the absorbent core 12. In other words, the density of the absorbent core 12 is greater than the density of the acquisition distribution layer 18 and the density of the acquisition distribution layer 18 is greater than the density of the topsheet 14.

For example, the density of the topsheet 14 is comprised between 10 000 $g \cdot m^{-3}$ and 40 000 $g \cdot m^{-3}$, preferably between 15 000 $g \cdot m^{-3}$ and 30 000 $g \cdot m^{-3}$. The density of the ADL 18 is comprised between 60 000 $g \cdot m^{-3}$ and 112 000 $g \cdot m^{-3}$, preferably between 80 000 $g \cdot m^{-3}$ and 110 000 $g \cdot m^{-3}$. The density of the absorbent core 12 is comprised between 110 000 $g \cdot m^{-3}$ and 150 000 $g \cdot m^{-3}$, preferably between 112 000 $g \cdot m^{-3}$ and 130 000 $g \cdot m^{-3}$. As indicated by the examples, the density of ADL 18 is 2; 2.1; 2.2; 2.3; 2.4; 2.5; 2.6; 2.7; 2.8; 2.9; 3; 3.1; 3.2; 3.3; 3.4; 3.5; 3.6; 3.7; 3.8; 3.9; 4; 4.1; 4.2; 4.3; 4.4; 4.5; 4.6; 4.7; 4.8; 4.9; 5; 5.1; 5.2; 5.3; 5.4; 5.5; 5.6; 5.7; 5.8; 5.9; 6; 6.1; 6.2; 6.3; 6.4; 6.5; 6.6; 6.7; 6.8; 6.9; 7; 7.1; 7.2; 7.3; 7.4; 7.5; 7.6; 7.7; 7.8; 7.9 or more times greater than the density of the topsheet 14. The density of the absorbent core 12 is 1.1; 1.2; 1.3; 1.4; 1.5; 1.6; 1.7, 1.8; 1.9; 2; 2.1; 2.2; 2.3; 2.4; 2.5; 2.6; 2.7; 2.8; 2.9; 3 or more times greater than the density of the acquisition distribution layer 18.

Air Permeability Test Method

The following test method is performed to measure the air permeability (or "relative porosity" as referred to herein) of nonwoven substrates.

Equipment to be used: Air Permeability Tester Model FX 3300 LABOTESTER III (from Textest AG) fitted with a test head having part number FX 3300-20 (from Textest AG).

Procedure: Each nonwoven sample is placed (by using the respective clamping holder in the equipment) as an obstacle in a flow of air. A pressure difference $\Delta p$ (between both upper and lower faces of the nonwoven sample) develops as a consequence of hydraulic losses. The pressure difference is recorded by using of the manometer. Standard evaluation (according to EN ISO 9237:1995) is taken under the conditions: clamping area 20 cm², pressure difference 200 Pa. The measured value may be reported as a speed of air in litre per squared meters per second (L/m²/s).

It is supposed that the present invention is not restricted to any form of realization described previously and that some modifications can be added to the presented example of fabrication without reappraisal of the appended claims.

The invention claimed is:

1. An absorbent article (10) comprising an absorbent core (12) arranged between a liquid permeable topsheet (14) and a liquid impermeable backsheet (16), and an acquisition distribution layer (18) arranged between said topsheet (14) and said absorbent core (12), wherein the absorbent core (12) comprises at least an absorbent material layer, characterized in that the topsheet (14) consists essentially of an air-through bonded nonwoven layer and is free of spunbond nonwoven layers, in that the acquisition distribution layer (18) comprises a spunbonded and/or thermocarded nonwoven layer and in that the absorbent core (12) comprises at least one channel (26) free of absorbent material.

2. Absorbent article (10) according to claim 1, wherein the spunbonded layer of the acquisition distribution layer (18) is part of a multi-layer composite sheet additionally comprising a web of meltblown fibers.

3. Absorbent article (10) according to claim 1, wherein the acquisition distribution layer (18) is free of air-through bonded nonwoven layers.

4. Absorbent article (10) according to claim 1, wherein the acquisition distribution layer (18) is free of spunlaced nonwoven layers.

5. Absorbent article (10) according to claim 1, wherein each of the topsheet (14), acquisition distribution layer (18), and absorbent core (12) have an air permeability and wherein the air permeability of the topsheet (14) is greater than the air permeability of the acquisition distribution layer (18) and the air permeability of the acquisition distribution layer (18) is greater than the air permeability of the absorbent core (12).

6. Absorbent article (10) according to claim 5, wherein the acquisition distribution layer (18) has an air permeability of from 1 000 $L/m^2/s$ to 7 000 $L/m^2/s$.

7. Absorbent article (10) according to claim 5, wherein the topsheet (14) has an air permeability of from 4 000 $L/m^2/s$ to 12 000 $L/m^2/s$.

8. Absorbent article (10) according to claim 5, wherein the air permeability of the topsheet (14) is 1.1 times greater than the air permeability of the acquisition distribution layer (18)

and the air permeability of the acquisition distribution layer (18) is 1.1 times greater than the air permeability of the absorbent core (12).

9. Absorbent article (10) according to claim 1, wherein each of the topsheet (14), acquisition distribution layer (18), and absorbent core (12) have a mean flow pore size and wherein the mean flow pore size of the topsheet (14) is greater than the mean flow pore size of the acquisition distribution layer (18) and the mean flow pore size of the acquisition distribution layer (18) is greater than the mean flow pore size of the absorbent core (12).

10. Absorbent article (10) according to claim 1, wherein the topsheet air-through bonded nonwoven layer is the most exterior layer of a body-facing side of the absorbent article, adapted to be in contact with the skin when the absorbent article is worn.

11. Absorbent article (10) according to claim 1, wherein the at least one channel (26) is an interconnected channel forming a substantially continuous path.

12. Absorbent article (10) according to claim 1, wherein each of the topsheet (14), acquisition distribution layer (18), and absorbent core (12) have a density and wherein the density of the topsheet (14) is lesser than the density of the acquisition distribution layer (18) and the density of the acquisition distribution layer (18) is lesser than the density of the absorbent core (12).

\* \* \* \* \*